United States Patent
Sangild

(10) Patent No.: US 9,572,365 B2
(45) Date of Patent: Feb. 21, 2017

(54) BOVINE COLOSTRUM AS MINIMAL ENTERAL NUTRITION FOR PRETERM INFANTS

(71) Applicant: KØBENHAVNS UNIVERSITET, Copenhagen K (DK)

(72) Inventor: Per Torp Sangild, Copenhagen NV (DK)

(73) Assignee: KØBENHAVNS UNIVERSITET, Copenhagen K (DK)

( * ) Notice: Subject to any disclaimer, the term of this patent is extended or adjusted under 35 U.S.C. 154(b) by 0 days.

(21) Appl. No.: 14/405,848

(22) PCT Filed: Jun. 7, 2013

(86) PCT No.: PCT/DK2013/050184
§ 371 (c)(1),
(2) Date: Dec. 5, 2014

(87) PCT Pub. No.: WO2013/182207
PCT Pub. Date: Dec. 12, 2013

(65) Prior Publication Data
US 2015/0216212 A1    Aug. 6, 2015

(30) Foreign Application Priority Data

Jun. 7, 2012 (DK) .................................. 2012 70309

(51) Int. Cl.
*A23L 1/29* (2006.01)
*A61K 35/20* (2006.01)

(52) U.S. Cl.
CPC ................ *A23L 1/296* (2013.01); *A23L 33/40* (2016.08); *A61K 35/20* (2013.01)

(58) Field of Classification Search
None
See application file for complete search history.

(56) References Cited

PUBLICATIONS

Moller, Bovine colostrum is superior to enriched formulas in stimulating intestinal function and necrotising enterocolitis resistance in preterm pigs. The British journal of nutrition, (Jan. 2011) vol. 105, No. 1, pp. 44-53. Electronic Publication Date: Aug. 20, 2010.*

International Search Report for International Application No. PCT/DK2013/050184 dated Aug. 19, 2013.

Ostergaard et al., "Modulation of Intestinal Inflammation by Minimal Enteral Nutrition With Amniotic Fluid in Preterm Pigs" Journal of Parenteral and Enteral Nutrition, vol. Advanced Publication, pp. 1-11, May 28, 2013.

Cilieborg et al., "Diet-Dependent Effects of Minimal Enteral Nutrition of Intestinal Function and Necrotizing Enterocolitis in Preterm Pigs" Journal of Parenteral and Enteral Nutrition, vol. 35, No. 1, pp. 32-42, Jan. 2011.

Stoy AFC, et al. "Bovine colostrum improves intestinal function following formula-induced gut inflammation in preterm pigs" Clinical Nutrition (2013), http://dx.doi.org/10.1016/j.clnu.2013.05.013.

Moller et al., "Bovine colostrum is superior to enriched formulas in stimulating intestinal function and necrotising enterocolitis resistance in preterm pigs" British Journal of Nutrition, vol. 105, pp. 44-53, 2011.

* cited by examiner

*Primary Examiner* — Qiuwen Mi
(74) *Attorney, Agent, or Firm* — Harness, Dickey & Pierce, P.L.C.

(57) ABSTRACT

The invention relates to a product consisting of bovine colostrum for use in a method for minimal enteral nutrition for preterm infants, which product is given according to a specified dosage regime, while supplemental nutrients are supplied by total parenteral nutrition during at least the chief part of the treatment period. In a second aspect is provided the use of said product as minimal enteral nutrition for preterm infants according to the first aspect of the invention.

22 Claims, No Drawings

BOVINE COLOSTRUM AS MINIMAL ENTERAL NUTRITION FOR PRETERM INFANTS

CROSS-REFERENCE TO RELATED APPLICATIONS

This application is a 371 U.S. National Stage of International Application No. PCT/DK2013/050184, filed Jun. 7, 2013, and published in English as WO 2013/182207 A1 on Dec. 12, 2013, which claims priority to Danish Patent Application No. PA 2012 70309, filed Jun. 7, 2012. The entire disclosures of the above applications are incorporated by reference herein.

The present invention relates to a product consisting of bovine colostrum for use in a method for minimal enteral nutrition for preterm infants.

Preterm birth occurs in 10% of all births worldwide (Simmons et al., 2010) and is the leading cause of death for 3.1 mio. infants per year (Oestergaard et al., 1990). During the neonatal period (the first 4 weeks), immaturity of the gastrointestinal tract typically prevents uptake of a normal level of milk nutrients, and the ensuing slow growth is associated with negative effects on later health outcomes (Moster et al., 2008; Stephens et al., 2009).

The low digestive capacity in preterm infants is clinically manifested by intolerance to enteral food (vomiting, gut dysmotility, gastric residuals, and abdominal distension). Too rapid advancement of enteral feeding is associated with damage to the gut epithelium, bacterial overgrowth and increased risk of the serious gut inflammatory disorder necrotizing enterocolitis (NEC, Berseth et al., 2003).

After birth, preterm infants therefore often need intravenous nutrition (parenteral nutrition, PN) for 1-4 weeks to promote survival, nutrient uptake and growth. It is important, however, that the transition to enteral milk feeding occurs as soon as possible, because long term PN feeding is expensive, requires hospitalisation, and is associated with gut and metabolic problems (Bombell & McGuire, 2009; Siggers et al., 2011). Finally, PN will never be able to supply the amount of nutrients believed to be optimal for the growth of preterm infants. Uptake of milk nutrients via a well-functioning gut is required and a low protein intake could be a main reason for unnecessary growth restriction of preterm infants (Stephens et al., 2009; Ziegler et al., 2011).

The transition to enteral feeding with milk (from mother, human milk bank or infant formula) occurs at 0-14 days after birth. Some babies reach full enteral feeding already after a week, but others not until several weeks after birth. These differences partly depend on birth weight and gestational age at birth, but even for similar infants, feeding procedures vary widely among hospitals. Nevertheless, it is recognized that enteral feeding is important for infant growth and development but there are disagreements with regards to how a rapid transition to enteral feeding is best achieved.

The terms "minimal enteral nutrition" (MEN) and "trophic feeding" relate to a procedure, whereby the immature gastrointestinal system of preterm infants is primed with minute volumes of feeds in order to exert a beneficial trophic effect on the intestinal mucosa. Moreover, MEN has been associated with favourable muscular, vascular and endocrine responses, and the procedure is used as a preventive therapy against severe disorders, which otherwise tend to arise in the immature gut of preterm infants. The preferred feed for minimal enteral nutrition up to now has been human breast milk. However, there has been relatively little focus on the nature of the diet for preterm infants. While it is well recognized that mother's milk has benefits over infant formula (Ziegler et al., 2011), it is not known what the optimal formula composition is, when adequate mother's milk is not available, which is often the case for preterm infants around the world. Likewise, there are indications that increasing the nutrient intake from mother's milk by adding artificial formulas may actually have adverse effects (Sullivan et al., 2011). On the other hand, increasing nutrient intake, especially of protein, is consistently associated with better long term health outcome for very small and preterm infants (Stephens et al., 2009).

Colostrum, which is the first milk produced by mammals in late pregnancy and immediately after birth, has been proposed in its bovine variant as a dietary supplement for children and adults alike due to its high content of protein, antibodies and antimicrobial factors.

Thus, US 2004137073 describes the use of bovine colostrum to enhance immune response in a human subject, while WO 1999/56758 discloses a food composition containing colostrum, used for enhancing i.a. physical work capacity. The patent GB467825 relates to the use of colostrum for promoting the growth of infants, whereas WO2010095130 describes a nutritional composition comprising prolactin, which may be derived from colostrum. EP 1803358 A1 discloses a nutritional composition or infant formula comprising colostrum or a colostrum-derived product and a prebiotic component selected among galactoooligosaccharides, inulin, and a mixture thereof.

Sangiorgi (Rivista di clinica pediatrica, (1959 December) Vol. 64, pp. 574-87) reports a study on ingestion by premature infants of a constant, very high dose of fractionated bovine colostrum from day 3 after birth. Due to these dosage features, the feeding of colostrum cannot be considered a minimal enteral nutrition scheme, and in fact it turns out that no significant weight gain in the studied infants was achieved during the experimental period.

It has been found that bovine colostrum in many respects is similar to porcine colostrum and is more effective in protecting the gut and supporting body growth of piglets than traditional enriched formulas (Bjørnvad et al., 2008; Møller et al., 2011). However, while the findings regarding the response of piglets to bovine colostrum are supportive for effects also in preterm infants, they cannot be directly translated to a dosage regime for preterm infants for whom mother's milk may not be available. A number of factors make it impossible to directly infer from one of the species to the other. In children, hitherto only the general observation has been made that bovine colostrum is tolerated by individuals with a compromised gastrointestinal system following intestinal resection (Aunsholt et al., 2012).

The gastrointestinal tracts of piglets and infants, respectively, are not identical with regard to their anatomy and physiology during development, and this will inevitably affect the response to feeding bovine colostrum just after preterm birth (Sangild, 2006). As opposed to the newborn infant, the newborn pig shows low acid secretion and high chymosin secretion in the stomach, meaning that the process of milk casein clotting differs between the two species. This in turn will affect transit time and tolerance to large amounts of casein-containing bovine colostrum.

The piglet has a genetic predisposition for body growth that is much faster than in infants, making the physiological requirement for dietary amino acids much higher, relative to infants. On the other hand, excessive amino acid intake for too long may be toxic to the developing kidneys, liver and brain, especially in sensitive preterm newborns. Finally, the degree of gastrointestinal and metabolic development will differ widely between different gestational ages at delivery for both piglets and infants.

Based on the experience with piglets, giving bovine colostrum at the wrong time, or in the wrong amounts or wrong formulation will provide no benefit or, in the worst case, detrimental effects, relative to standard feeding protocols. A too early and/or too large dose is at the risk of overfeeding with ensuing bacterial owergroth and food intolerance, which may lead to the abovementioned serious condition of tissue necrosis and intestinal inflammation known as necrotizing enterocolitis. On the other hand, a too late and/or insufficient administration of bovine colostrum, where the feeding for a period will rely on parenteral nutrition alone, may result in a more vulnerable gastrointestinal tract with a decreased digestive and absorptive capacity as well as more pathogenic microbiota and thereby a predisposition for necrotizing enterocolitis. Therefore, a very delicate balance must be struck when establishing a dosage regime for preterm infants that will secure maximal effect and avoid negative side effects.

In view of the above, the object of the present invention is to provide a bovine colostrum dosage regime, whereby said bovine colostrum can be used as an effective minimal enteral nutrition in preterm infants, so that medical problems related to immaturity of the gastrointestinal tract may be prevented or alleviated. The applied product and dosage regime should furthermore be safe and affordable.

To meet this object, a product is provided, consisting of bovine colostrum for use in a method for minimal enteral nutrition for preterm infants, said colostrum being orally administered in the form of an unmodified product or as substantially reconstituted to its original concentration, starting from the day of birth in a dose of 5-27 mL/kg/day on day 1, followed by a dose of 13-27 mL/kg/day on day 2, and a dose of 21-35 mL/kg/day on day 3, and a dose of 29-35 mL/kg/day on day 4, and a dose of 37-43 mL/kg/day on day 5, and a dose of 37-51 mL/kg/day on day 6, and a dose of 29-43 mL/kg/day on day 7, and a dose of 13-43 mL/kg/day on day 8, while supplemental nutrients are supplied by total parenteral nutrition during the entire period. The colostrum product as substantially reconstituted to its original concentration preferably is obtained by admixing 15-20 g, preferably 17 g, of gently processed colostrum powder per 100 mL of water.

Based on the realization that preterm infants share the immature and immunodeficient state of newborn calves in contrast to normal infants, the inventor has established the above dosage regime for bovine colostrum, so that bovine colostrum may henceforth be successfully used in a program of trophic feeding of preterm infants over the first 8 days after birth. Although the chief part of the required nourishment with regard to energy is provided by the concomitant parental nutrition, the enteral feeding with colostrum also procures a fraction of the required nutrients. In this way the gastrointestinal tract is propitiously stimulated to maintain and develop its nutrient absorptive capacity, whereas the occurrence of necrotizing enterocolitis is minimized.

According to a preferred embodiment, said colostrum is orally administered in the form of an unmodified product or as substantially reconstituted to its original concentration, starting from the day of birth in a dose of 5-11 mL/kg/day, preferably 8 mL/kg/day, on day 1, followed by a dose of 13-19 mL/kg/day, preferably 16 mL/kg/day, on day 2, and a dose of 21-27 mL/kg/day, preferably 24 mL/kg/day, on day 3, and a dose of 29-35 mL/kg/day, preferably 32 mL/kg/day, on day 4, and a dose of 37-43 mL/kg/day, preferably 40 mL/kg/day, on day 5, and a dose of 45-51 mL/kg/day, preferably 48 mL/kg/day, on day 6, and a dose of 29-35 mL/kg/day, preferably 32 mL/kg/day, on day 7, and a dose of 13-19 mL/kg/day, preferably 16 mL/kg/day, on day 8, while supplemental nutrients are supplied by total parenteral nutrition during the entire period. This dosage regime represents a careful compromise between feeding enough bovine colostrum to help mature the immature gastrointestinal tract and help supply amino acids and other nutrients for growth from shortly after birth, and the consideration not to feed too much, too early and for too long, before transition to other milk diets (infant formula or human milk).

In an alternative embodiment, said colostrum is orally administered in the form of an unmodified product or as substantially reconstituted to its original concentration, starting from the day of birth in a dose of 21-27 mL/kg/day, preferably 24 mL/kg/day, on days 1 and 2, followed by a dose of 29-35 mL/kg/day, preferably 32 mL/kg/day, on days 3 and 4, and a dose of 37-43 mL/kg/day, preferably 40 mL/kg/day, on days 5 to 8, while supplemental nutrients are supplied by total parenteral nutrition during the entire period. This also represents a useful dosage regime.

The invention may thus be used for prevention of gut-related and metabolic disorders.

Preferably, the bovine colostrum is administered every 3 hours as slow bolus feeding over a period of 2-5 minutes. Thus, an intermittent but still frequent feeding is provided that aims to prime the gastrointestinal system without overloading it and to some extent also mimic the eating pace a child would normally set. Individual children not able to tolerate this feeding regime, as indicated by vomiting, extensive gastric residuals or other adverse clinical or metabolic effects, would have to continue lower feeding volumes for more days before volume advancement.

According to a preferred embodiment, said colostrum is only given up to and including day 8, whereafter it is fully replaced by infant formula or human breast milk from day 9 after birth. The human breast milk may be banked human milk fed by enteral tube or bottle, or human milk from their own mother.

Preferentially, said colostrum is given as sole enteral nutrition during the first 6 days.

Advantageously, said colostrum is in the form of an integral, unfractionated product, which has not been subjected to pasteurisation, and which has been obtained from healthy dairy cows, preferably of Holstein-Friesian breed, advantageously only from the first and second milking after parturition. Colostrum from Jersey cows is often even richer in protein including immunoglobulins and may also come into consideration.

In a preferred embodiment, the bovine colostrum is not administered as part of a composition further comprising galactooligosaccharides, inulin or any components derived from the human body. In order not to stress the gastrointestinal system of the preterm infants, colostrum should preferentially be given alone as the only oral ingestion for most of the duration of the protocol of minimal enteral nutrition, until colostrum is finally stepped down to be replaced by infant formula or human breast milk.

Favourably, said colostrum enters into an overall nutrient dosage regime as specified in Claim 7. On day 13, an enteral feed intake of approximately 150 mL/kg/day is reached, and on this point the infant should preferably be in the process of weaning off from parenteral nutrition if not already weaned off.

According to an alternative embodiment, said colostrum enters into an overall nutrient dosage regime as specified in claim 8.

To meet the aforementioned object, according to a second aspect of the invention the use of a product consisting of bovine colostrum as minimal enteral nutrition for preterm infants according to any one of the preceding claims is provided. Said use provides the same advantages as the first aspect of the invention.

In the following, an overall description of a preferred embodiment of the invention will now be given in more details.

A preterm infant in need of minimal enteral nutrition is given the necessary equipment for parenteral nutrition and for bolus feeding, which is batchwise feeding through an enteral feeding tube. An amount of enteral milk in the form of bovine colostrum must be given already within few hours of birth (2-4 hours) to stimulate intestinal peristalsis, digestive development and to avoid unnecessary gut fasting that will more easily lead to bacterial dyscolonisation. Bovine colostrum should be used as a trophic feed but also partly supplying nutrients, over the first 8 days after birth. Remaining nutrients are supplied by total parenteral nutrition as specified in Claim 7. The start dose of bovine colostrum is 1 mL/kg/3 hours (8 mL/kg/day) given as slow bolus feeding over 2-3 min. Each day this level is increased by 1 mL/kg/3 hours until reaching approximately 48 mL/kg/day (16 mL/kg/day on day 2; 24 mL/kg/day on day 3; 32 mL/kg/day on day 4; 40 mL/kg/day on day 5; 48 mL/kg/day on day 6). Thereafter, bovine colostrum is stepped down (32 mL/kg/day on day 7; 16 mL/kg/day on day 8). On approximately day 9, bovine colostrum is fully replaced with infant formula or human banked milk or with breast feeding from own mother, starting from approximately day 7, to reach approximately at day 13 an enteral feed intake of 150 mL/kg/day. As soon as tolerated, the infant should be weaning off from parenteral nutrition and the enteral diet should be changed entirely to the follow-on diet, either breast feeding, human donor milk (with or without fortifiers), or infant formula of the perceived optimal quality.

Bovine colostrum should be given as the raw, intact and near-normal undiluted product, or reconstituted with water to the near-normal concentration from a powdered product. When reconstituted from powder, 17 g of colostrum powder per 100 mL of sterile water at 20-30° C. is mixed and warmed to 36-39° C. just before each feeding. The bovine colostrum thus reconstituted will have a similar energy content to that of reconstituted infant formula. There is evidence to suggest that fractions of colostrum will not be as effective as the entire product where all the bioactive substances work in synergy to secure adequate nutrient uptake, growth, gut protection and maturation.

Apart from a short transition period of a couple of days when stepping down colostrum, it should preferably not be used as an adjunct simultaneously with other milks or formulas. This is to avoid the risk of disturbance of the intestinal colostrum bioactivity and gastric clotting process. Because bovine colostrum works in a complex matrix of effects, both within the different components of colostrum, and with the immature gut immune system and bacterial composition, this food matrix must be maintained to achieve efficacy for this sensitive system. The gut needs to carefully adapt itself to the bioactivity of colostrum, and this adaptation process should preferentially not be disturbed by other enteral food products.

The bovine colostrum in this embodiment is obtained only from the first and second milking after parturition in healthy dairy cows of Holstein-Friesian breed. This is to maintain the highest level of bioactivity in the samples. In the present embodiment, the bovine colostrum is reconstituted to its original concentration from colostrum powder, which is produced by gentle low-temperature techniques. It is sterilized, not by pasteurisation, but by mild gamma irradiation, and is gently spray-dried to preserve bioactivity. Tolerance of the part of the infant to colostrum feeding is carefully monitored by registration of gastric aspirations, abdominal palpation and circulating blood urea levels (to follow urinary nitrogen excretion, <15 mmol/L urea). It is important that feeding with colostrum is continued, unless there is excessive vomiting and residuals.

The diet and infusion rate of parenteral nutrition is similar to that of preterm infants that would traditionally not receive colostrum minimal enteral nutrition or that would normally receive a formula product as the first diet. During the first week after birth, protein intake may exceed the normal requirement for preterm babies of 3-4 g/kg/d. Part of this protein is supplied via the gut and +20% extra protein requirement from the enteral source is related to low digestive capacity as well as increased gut protein metabolism following enteral feeding.

The treatment proceeds according to the feeding protocol specified in Claim 7, which protocol has been found to be the optimal one, using bovine colostrum during the first 8 days after birth in combination with parenteral nutrition, where colostrum enters as the only enteral diet for the first 6 days after birth. Thus, optimal care is provided for the immature gut, taking into account digestive dysfunction, unstable microbiology as well as immature gut immunology.

In the absence of maternal human milk for preterm babies, bovine colostrum has turned out to be the best possible substitute as trophic feed throughout the first week after birth, when supplied in proper doses. The reasons that are believed to underlie the successful application of bovine colostrum as a minimal enteral nutrition product for preterm infants could finally be summarized as follows:

High concentrations of numerous antimicrobial, growth and immodulatory factors that will aid in gut maturation and protection against inflammatory reactions; a high concentration of a readily available whey protein source, which is a key to facilitate superior body growth and development over the first week relative to a diet based on PN alone; and the possibility to prepare bovine colostrum as a sterile, gently heat-treated powder with maximal protection of all milk proteins, which will help to secure more satisfactory effects relative to infant formula.

REFERENCES

Aunsholt L, Jeppesen P B, Lund P, Sangild P T, Ifaoui I B, Qvist N, Husby S. (2012). Bovine colostrum to children with short bowel syndrome: A randomized, double-blind, crossover pilot study. JPEN J Parenter Enteral Nutr.

Berseth C L, Bisquera J A, Paje V U. Prolonging small feeding volumes early in life decreases the incidence of necrotizing enterocolitis in very low birth weight infants. Pediatrics. 2003 111:529-34.

Bjornvad C R, Thymann T et al. Enteral feeding induces diet-dependent mucosal dysfunction, bacterial proliferation, and necrotizing enterocolitis in preterm pigs on parenteral nutrition. Am J Physiol Gastrointest Liver Physiol. 2008 295(5):G1092-103.

Bombell S, McGuire W. Early trophic feeding for very low birth weight infants. Cochrane Database Syst Rev. 2009 8; (3):CD000504

Moster D, Lie R T, Markestad T. Long-term medical and social consequences of preterm birth. N Engl J Med. 2008, 359:262-73.

Møller H K, Thymann T et al. Bovine colostrum is superior to enriched formulas in stimulating intestinal function and necrotising enterocolitis resistance in preterm pigs. Br J Nutr. 2011 105:44-53.

Oestergaard M Z, Inoue M et al. Neonatal mortality levels for 193 countries in 2009 with trends since 1990: a systematic analysis of progress, projections, and priorities. PLoS Med. 2011 8:e1001080.

Quigley M A, Henderson G et al. Formula milk versus donor breast milk for feeding preterm or low birth weight infants. Cochrane Database Syst Rev. 2007 Oct. 17; (4):CD002971.

Sangild P T. Gut responses to enteral nutrition in preterm infants and animals. Exp Biol Med 2006; 231(11):1695-711.

Simmons L E, Rubens C E et. al. Preventing preterm birth and neonatal mortality: exploring the epidemiology, causes, and interventions. Semin Perinatol. 2010 34:408-15.

Stephens B E, Walden R V, Gargus R A, Tucker R, McKinley L, Mance M, Nye J, Vohr B R. First-week protein and energy intakes are associated with 18-month developmental outcomes in extremely low birth weight infants. Pediatrics. 2009 123:1337-43.

Sullivan S, Schanler R J et al. An exclusively human milk-based diet is associated with a lower rate of necrotizing enterocolitis than a diet of human milk and bovine milk-based products. J Pediatr. 2010 156:562-7.

Ziegler E E. Meeting the nutritional needs of the low-birth-weight infant. Ann Nutr Metab. 2011; 58 Suppl 1:8-18. Epub 2011 Jun. 21.

The invention claimed is:

1. A method for minimal enteral nutrition for preventing severe disorders in the immature gut of preterm infants, wherein bovine colostrum is orally administered in the form of an unmodified product or as substantially reconstituted to its original concentration, starting from the day of birth in a dose of 5-27 mL/kg/day on day 1, followed by a dose of 13-27 mL/kg/day on day 2, and a dose of 21-35 mL/kg/day on day 3, and a dose of 29-35 mL/kg/day on day 4, and a dose of 37-43 mL/kg/day on day 5, and a dose of 37-51 mL/kg/day on day 6, and a dose of 29-43 mL/kg/day on day 7, and a dose of 13-43 mL/kg/day on day 8, while supplemental nutrients are supplied by total parenteral nutrition during the entire period.

2. The method according to claim 1, wherein said colostrum is orally administered in the form of an unmodified product or as substantially reconstituted to its original concentration, starting from the day of birth in a dose of 5-11 mL/kg/day on day 1, followed by a dose of 13-19 mL/kg/day on day 2, and a dose of 21-27 mL/kg/day on day 3, and a dose of 29-35 mL/kg/day on day 4, and a dose of 37-43 mL/kg/day on day 5, and a dose of 45-51 mL/kg/day on day 6, and a dose of 29-35 mL/kg/day on day 7, and a dose of 13-19 mL/kg/day on day 8, while supplemental nutrients are supplied by total parenteral nutrition during the entire period.

3. The method according to claim 1, wherein said colostrum is orally administered in the form of an unmodified product or as substantially reconstituted to its original concentration, starting from the day of birth in a dose of 21-27 mL/kg/day on days 1 and 2, followed by a dose of 29-35 mL/kg/day on days 3 and 4, and a dose of 37-43 mL/kg/day on days 5 to 8, while supplemental nutrients are supplied by total parenteral nutrition during the entire period.

4. The method according to claim 1, wherein said method is for use in prevention of gut-related and metabolic disorders.

5. The method according to claim 1, wherein said colostrum is administered every 3 hours as slow bolus feeding over a period of 2-5 minutes.

6. The method according to claim 1, wherein said colostrum is only given up to and including day 8.

7. The method according to claim 1, wherein said colostrum is given as sole enteral nutrition during the first 6 days.

8. The method according to claim 1, wherein said colostrum is in the form of an integral, unfractionated product, which has not been subjected to pasteurisation, and which has been obtained from healthy dairy cows, advantageously only from the first and second milking after parturition.

9. The method according to claim 1, wherein said colostrum enters into the following overall nutrient dosage regime:

| Day (Day 1 = day of birth) | Parenteral nutrition mL/kg/day | Bovine colostrum mL/kg/day | Infant formula (or human breast milk) mL/kg/day | Total mL/kg/day |
|---|---|---|---|---|
| 1 | 62 | 8 | — | 70 |
| 2 | 74 | 16 | — | 90 |
| 3 | 86 | 24 | — | 110 |
| 4 | 88 | 32 | — | 120 |
| 5 | 90 | 40 | — | 130 |
| 6 | 92 | 48 | — | 140 |
| 7 | 86 | 32 | 32 | 150 |
| 8 | 70 | 16 | 64 | 150 |
| 9 | 54 | — | 96 | 150 |
| 10 | 38 | — | 112 | 150 |
| 11 | 22 | — | 128 | 150 |
| 12 | 6 | — | 144 | 150 |
| 13 | 0 | — | 150 | 150 |
| 14 | 0 | — | 150 | 150 |
| 15 | 0 | — | 150 | 150. |

10. The method according to claim 1, wherein said colostrum enters into the following overall nutrient dosage regime:

| Day (Day 1 = day of birth) | Parenteral nutrition mL/kg/day | Bovine colostrum mL/kg/day | Infant formula (or human breast milk) mL/kg/day | Total mL/kg/day |
|---|---|---|---|---|
| 1 | 60 | 24 | — | 84 |
| 2 | 60 | 24 | — | 84 |
| 3 | 60 | 32 | — | 92 |
| 4 | 60 | 32 | — | 92 |
| 5 | 60 | 40 | — | 100 |
| 6 | 60 | 40 | — | 100 |
| 7 | 60 | 40 | — | 100 |
| 8 | 60 | 40 | — | 100 |
| 9 | 60 | — | 48 | 108 |
| 10 | 60 | — | 48 | 108 |
| 11 | 60 | — | 72 | 132 |
| 12 | 60 | — | 72 | 132 |
| 13 | 60 | — | 108 | 168 |
| 14 | 60 | — | 108 | 168 |
| 15 | 30 | — | 144 | 174. |

11. The method according to claim 2, wherein said colostrum is orally administered, starting from the day of birth in a dose of 8 mL/kg/day.

12. The method according to claim 2, wherein said colostrum is orally administered on day 2 in a dose of 16 mL/kg/day.

13. The method according to claim 2, wherein said colostrum is orally administered on day 3 in a dose of 24 mL/kg/day.

14. The method according to claim 2, wherein said colostrum is orally administered on day 4 in a dose of 32 mL/kg/day.

15. The method according to claim 2, wherein said colostrum is orally administered on day 5 in a dose of 40 mL/kg/day.

16. The method according to claim 2, wherein said colostrum is orally administered on day 6 in a dose of 48 mL/kg/day.

17. The method according to claim 2, wherein said colostrum is orally administered on day 7 in a dose of 32 mL/kg/day.

18. The method according to claim 2, wherein said colostrum is orally administered on day 8 in a dose of 16 mL/kg/day.

19. The method according to claim 3, wherein said colostrum is orally administered on days 1 and 2 in a dose of 24 mL/kg/day.

20. The method according to claim 3, wherein said colostrum is orally administered on days 3 and 4 in a dose of 32 mL/kg/day.

21. The method according to claim 3, wherein said colostrum is orally administered on days 5 through 8 in a dose of 40 mL/kg/day.

22. The method according to claim 8, wherein said colostrum is obtained from healthy dairy cows of the Holstein-Friesian breed.

* * * * *